(12) United States Patent
Mizrahy et al.

(10) Patent No.: US 8,545,523 B2
(45) Date of Patent: Oct. 1, 2013

(54) TISSUE REPAIR METHOD AND KIT

(75) Inventors: Moshe Mizrahy, Tel Aviv (IL); Ofir Rimer, Kfar Truman (IL); Nir Altman, Kibbutz Kfar Etzion (IL); Einat Fabian, Kfar Truman (IL)

(73) Assignee: EasyLap Ltd., Kfar Truman (IL)

( * ) Notice: Subject to any disclaimer, the term of this patent is extended or adjusted under 35 U.S.C. 154(b) by 763 days.

(21) Appl. No.: 12/484,258

(22) Filed: Jun. 15, 2009

(65) Prior Publication Data

US 2010/0318107 A1 Dec. 16, 2010

(51) Int. Cl.
*A61B 17/08* (2006.01)
*A61B 17/10* (2006.01)
*A61B 17/06* (2006.01)

(52) U.S. Cl.
USPC .............. 606/151; 606/139; 606/222; 600/30

(58) Field of Classification Search
USPC .................. 606/139, 144, 148, 151, 213–223
See application file for complete search history.

(56) References Cited

U.S. PATENT DOCUMENTS

| | | | |
|---|---|---|---|
| 5,304,187 A * | 4/1994 | Green et al. | 606/151 |
| 5,830,221 A * | 11/1998 | Stein et al. | 606/157 |
| 5,919,184 A * | 7/1999 | Tilton, Jr. | 606/1 |
| 6,257,241 B1 * | 7/2001 | Wampler | 128/898 |
| 6,416,486 B1 * | 7/2002 | Wampler | 601/2 |
| 6,425,900 B1 * | 7/2002 | Knodel et al. | 606/139 |
| 6,638,286 B1 * | 10/2003 | Burbank et al. | 606/157 |
| 7,431,725 B2 * | 10/2008 | Stack et al. | 606/151 |
| 7,867,222 B1 * | 1/2011 | Tilton et al. | 606/1 |
| 2003/0004544 A1 * | 1/2003 | Kawashima et al. | 606/222 |
| 2005/0096673 A1 * | 5/2005 | Stack et al. | 606/151 |
| 2005/0240260 A1 * | 10/2005 | Bolduc | 623/1.36 |
| 2006/0241622 A1 * | 10/2006 | Zergiebel | 606/73 |

FOREIGN PATENT DOCUMENTS

| | | |
|---|---|---|
| EP | 1990014 | 11/2008 |
| WO | 2008099382 | 8/2008 |
| WO | 2009069119 | 4/2009 |

OTHER PUBLICATIONS

PCT Search Report PCT/CN2010/074012.

* cited by examiner

*Primary Examiner* — Darwin Erezo
*Assistant Examiner* — Jing Ou
(74) *Attorney, Agent, or Firm* — Dekel Patent Ltd.; David Klein (57) ABSTRACT

A method for tissue repair including providing a kit including a mesh placer, mesh stitcher and mesh tacker, placing the mesh at a tissue repair site with the mesh placer, holding the mesh in place with the mesh placer, and fastening the mesh to tissue with at least one of the mesh tacker and mesh stitcher.

4 Claims, 8 Drawing Sheets

TISSUE REPAIR METHOD AND KIT

FIELD OF THE INVENTION

The present invention generally relates to a kit and method for the deployment and placement of a mesh-sheet in a body, such as for hernia repair in a laparoscopic procedure.

BACKGROUND OF THE INVENTION

Hernias are abnormal protrusions of an organ (or organs) through a defect or natural opening in a covering membrane, muscle or bone. Most hernias protrude in the inguinal region as inguinal (direct or indirect) or femoral hernias and in the anterior abdominal wall region, as incisional, umbilical, epigastric or Spigelian hernias.

Hernia repair may require surgery. A small defective gap may be closed by sutures, and in cases of a larger defective gap, a mesh-sheet (or mesh, for short) may be applied over the gap. In some cases a mesh-sheet may be used for reinforcing a primary sutured defect in the abdominal wall. The mesh-sheet is fixed with sutures at peripheral edges thereof to the abdominal wall.

Tools have been developed to assist deploying and placing mesh-sheets in a laparoscopic procedure. However, although mesh sheets are used in most hernia repair procedures today, in the prior art there has been no tool or accepted standard for deploying and placing the mesh laparoscopically.

SUMMARY OF THE INVENTION

The present invention seeks to provide a kit and method for the deployment and placement of a mesh-sheet in a body, e.g., the abdominal cavity or the inguinal space, such as for covering a hernial defect of a patient during a hernia repair in a laparoscopic procedure.

The term hernia is used throughout the specification and claims to encompass any type of hernia, such as but not limited to, abdominal hernia (incisional, umbilical, epigastric or Spigelian), inguinal hernia (inguinal or femoral) and others. It is noted that the invention is not limited to repair of hernias and may be used for any medical procedure that requires some kind of deployment of a mesh.

The present invention may be used for abdominal hernia repairs of any of the aforementioned types, e.g., incisional, umbilical, Spigelian and epigastric hernias. Moreover, it is appreciated that the invention is applicable in a variety of similar operations, such as, for example inguinal hernias, etc (direct and indirect) and femoral hernias.

There is thus provided in accordance with an embodiment of the present invention a kit for tissue repair including:

(A) a mesh placer including an application member that articulates with respect to a deployment rod, a mesh being attached to the application member, (B) a mesh stitcher for stitching the mesh to tissue, including a first puncture element including a sharp distal end for puncturing tissue, a second puncture element including a sharp distal end for puncturing tissue, the distal ends of the first and second puncture elements being spaced from each other by a gap, suture thread disposed along a portion of the first puncture element, wherein the suture thread is arranged to be grabbed at the distal end of the first puncture element, and a suture grabber positioned at the distal end of the second puncture element, the suture assembly having a mode of operation wherein:

a. the first puncture element punctures through a tissue wall so that the suture thread passes from a near side of the tissue wall to a far side of the tissue wall, b. the second puncture element punctures through the tissue wall from the near side to the far side of the tissue wall, and c. the suture grabber grabs the suture thread at the distal end of the first puncture element at the far side of the tissue wall, brings the suture thread across the gap and moves the suture thread proximally away from the distal end of the second puncture element back through to the near side of the tissue wall, and (C) a tacker for applying a rotary tack for tacking the mesh to tissue including a handle with a first trigger assembly and a second trigger assembly, the trigger assemblies being coupled to an articulated applicator arm which is disposed through a drive shaft connected to the handle, the first trigger assembly operative to apply a rotary tack from a distal end of the applicator arm and the second trigger assembly operative to bend the distal end of the applicator arm, wherein a longitudinal axis of the handle is tilted with respect to the drive shaft.

The suture grabber may be manipulated by a manipulator operable by one hand. The kit may further include a rotary tack disposed on the applicator arm. The rotary tack may include a helical body constructed of a resorbable material.

There is also provided in accordance with an embodiment of the present invention a method for tissue repair including providing a kit as described above, placing the mesh at a tissue repair site with the mesh placer, holding the mesh in place with the mesh placer, and fastening the mesh to tissue with at least one of the mesh tacker and mesh stitcher.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Reference is now made to FIGS. 1-5, which illustrate a mesh placer 10, constructed and operative in accordance with an embodiment of the present invention, which is part of the kit and method for mesh deployment of the present invention.

Mesh placer 10 may be similar in construction to the mesh deployment apparatus described in PCT Patent Application PCT/IL2008/000149 (and copending U.S. patent application Ser. No. 11/674,683), the disclosures of which are incorporated herein by reference.

Figure 1:
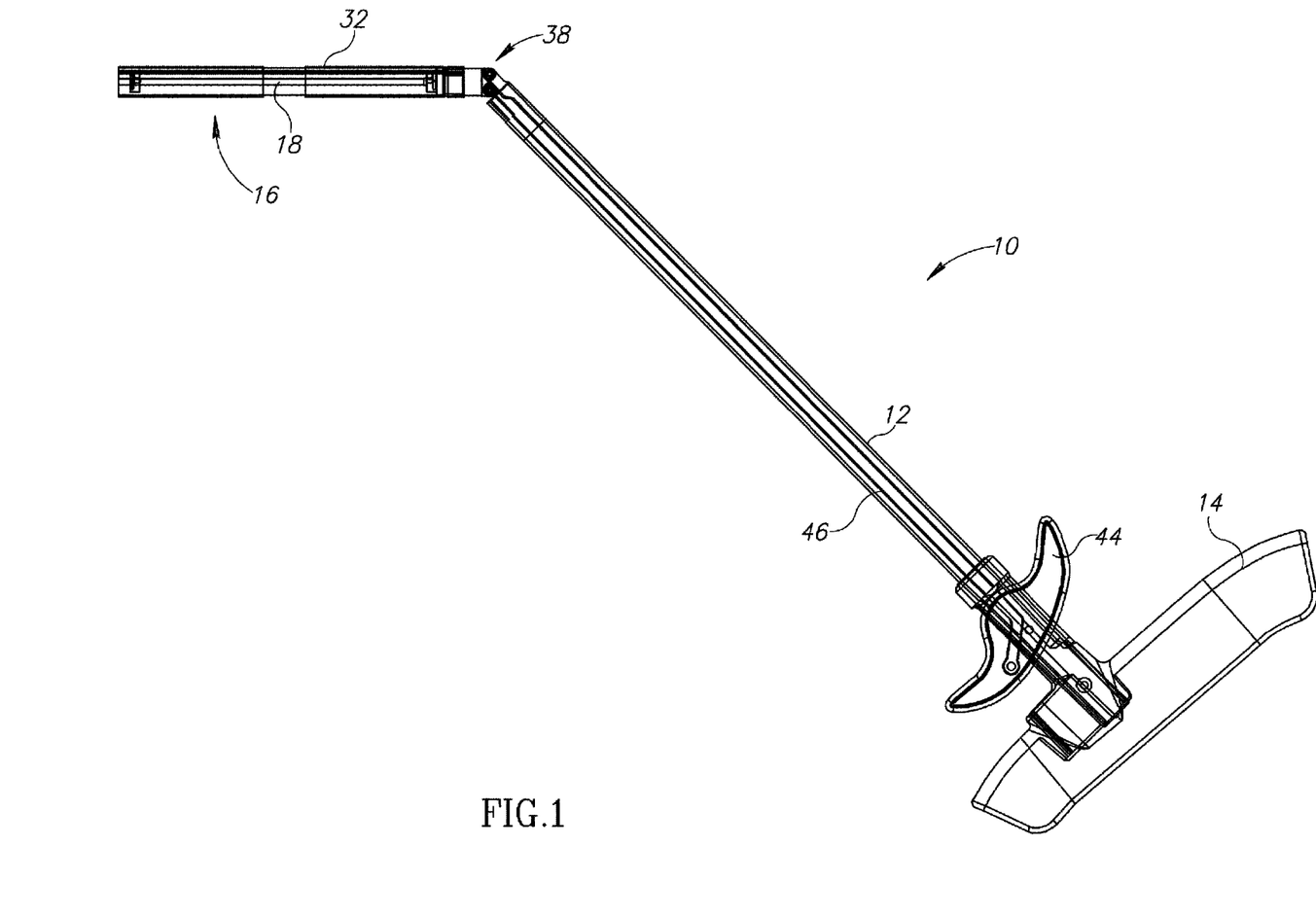
FIG. 1 is a simplified illustration of a mesh placer, constructed and operative in accordance with an embodiment of the present invention, which is part of the kit and method for mesh deployment of the present invention.
Figure 2:
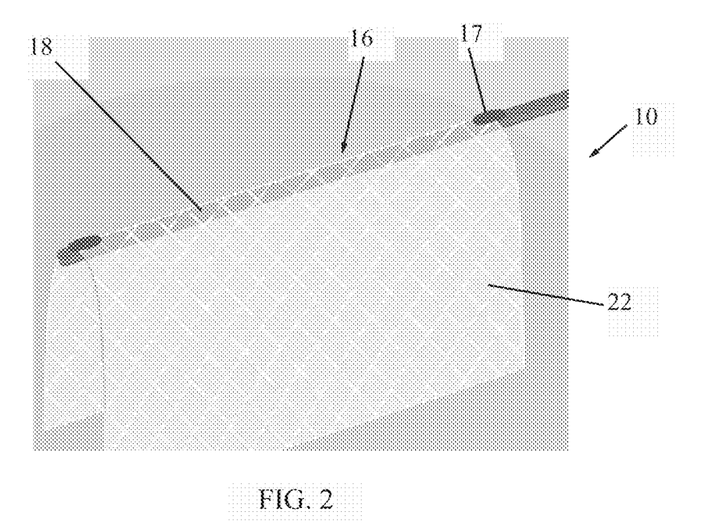
FIG. 2 is a simplified illustration of a mesh attached to the mesh placer, in accordance with an embodiment of the present invention.

Mesh placer 10 may include a deployment rod 12 having a handle 14 at a proximal portion thereof and an application member 16 at a distal portion thereof (FIG. 1). Application member 16 may include a shaft 18, which may be a rotating shaft as seen in FIG. 1, but not necessarily rotating, as seen in FIGS. 2-5. A mesh 22, made of a bio-compatible material as is well known in the art, is detachably attached to shaft 18 of application member 16 (FIG. 2). Shaft 18 is thus a mesh attachment member for attaching mesh 22 thereto.

As seen in FIG. 1, application member 16 may optionally be disposed in a cannula 32. Application member 16 may be articulated with respect to deployment rod 12 by means of a joint 38. In the non-limiting illustrated embodiment, the joint 38 is made up of two pinned connections between deployment rod 12 and roller portion 16.

A manipulating member 44 may be mounted on deployment rod 12. For example, manipulating member 44 may include a lever arm pivotedly mounted on deployment rod 12 and operatively connected to application member 16 by a linking member 46 (or alternatively, pulleys, gears or other mechanisms) that runs through a lumen formed in deployment rod 12. By pivoting manipulating member 44 (pulling either side of manipulating member 44 towards handle 14), the manipulating member 44 moves application member 16 about joint 38 to a position wherein application member 16 is not collinear with deployment rod 12.

The jointed connection of mesh placer 10 may enable placing mesh 22 in a patient with significantly greater dexterity and possibilities of motion that heretofore were not possible.

Figure 3:
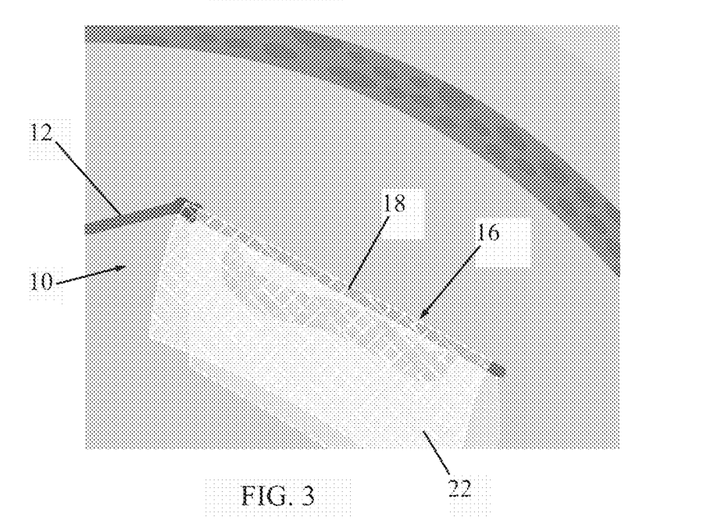
FIG. 3 is a simplified illustration of articulate the application member of the mesh placer, which curves to hold the mesh anatomically in place at the hernia site, in accordance with an embodiment of the present invention.
Figure 4:
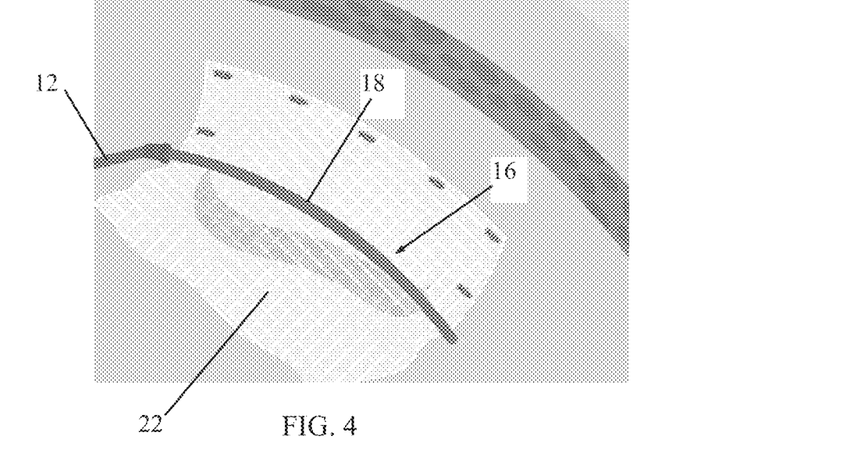
FIG. 4 is a simplified illustration showing flexibility of the application member of the mesh placer to center the mesh beneath the hernia site, in accordance with an embodiment of the present invention.
Figure 5:
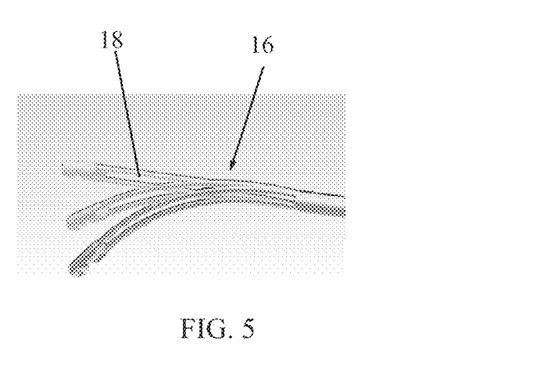
FIG. 5 is a simplified illustration showing that the flexibility of the application member enables adjustment to the abdominal wall curve, in accordance with an embodiment of the present invention.

FIG. 2 illustrates mesh 22 attached to mesh placer 10 and held in place, such as by means of resilient fingers 17. FIG. 3 illustrates articulating application member 16 of the mesh placer, wherein shaft 18 curves to hold mesh 22 anatomically in place at the hernia site. FIG. 4 illustrates the flexibility of the shaft 18 of application member 16 to center mesh 22 beneath the hernia site. FIG. 5 illustrates that the flexibility of application member 16 enables adjustment to the abdominal wall curve.

The mesh placer 10 facilitates laparoscopic introduction of the mesh 22 to the repair site and allows for optimal placement. Although mesh is used in most hernia repair procedures today, in the prior art there has been no tool or accepted standard for deploying and placing the mesh laparoscopically. The mesh placer 10 of the present invention can be used as a standard tool, enabling broader adoption of laparoscopic hernia repair by shortening the learning curve, reducing procedure time, optimizing techniques and minimizing complications.

Proper centering of mesh over an abdominal wall defect is challenging in laparoscopic procedures because maneuverability is limited. The mesh placer 10 gives the surgeon the flexibility needed to optimally center, position, and deploy the mesh.

Reference is now made to FIGS. 6-10, which illustrate a mesh stitcher 30, constructed and operative in accordance with an embodiment of the present invention, which is part of the kit and method for mesh deployment of the present invention.

Mesh stitcher 30 may be similar in construction to the suture assembly described in PCT Patent Application PCT/IL2008/001518 (and copending U.S. patent application Ser. No. 11/947,798), the disclosures of which are incorporated herein by reference.

Figure 6:
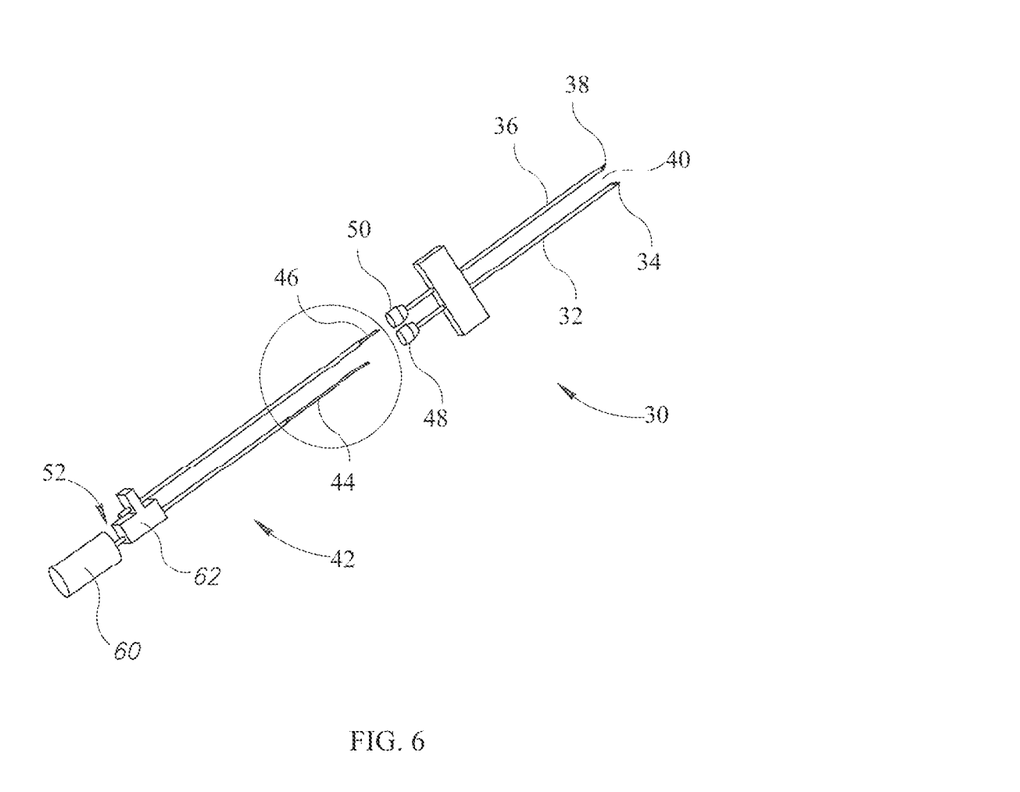
FIG. 6 is a simplified illustration of a mesh stitcher, constructed and operative in accordance with an embodiment of the present invention, which is part of the kit and method for mesh deployment of the present invention.

Mesh stitcher 30 includes a first puncture element 32 including a sharp distal end 34 for puncturing tissue, and a second puncture element 36 including a sharp distal end 38 for puncturing tissue. The distal ends 34 and 38 of first and second puncture elements 32 and 34 are spaced from each other by a gap 40. Preferably, but not necessarily, first and second puncture elements 32 and 34 are parallel to each other.

First and second puncture elements 32 and 36 are hollow. A suture manipulating assembly 42 that includes a suture thread receiving member 44 and a suture grabber 46, which can be passed into the hollow portions of first and second puncture elements 32 and 36, respectively. First and second puncture elements 32 and 36 are provided with distal funnel cups 48 and 50, respectively, for guiding insertion of suture thread receiving member 44 and suture grabber 46. The funnel cups 48 and 50 also serve as stops to limit movement of suture thread receiving member 44 and suture grabber 46 into first and second puncture elements 32 and 36. Proximal ends of suture thread receiving member 44 and suture grabber 46 are mounted on a handle assembly 52.

In the non-limiting illustrated embodiment, suture thread receiving member 44 is mounted to a one-handed manipulator 60 of handle assembly 52. Manipulator 60 is arranged for moving with respect to a block 62 of handle assembly 52 by means of a latch, for example.

Figure 7:
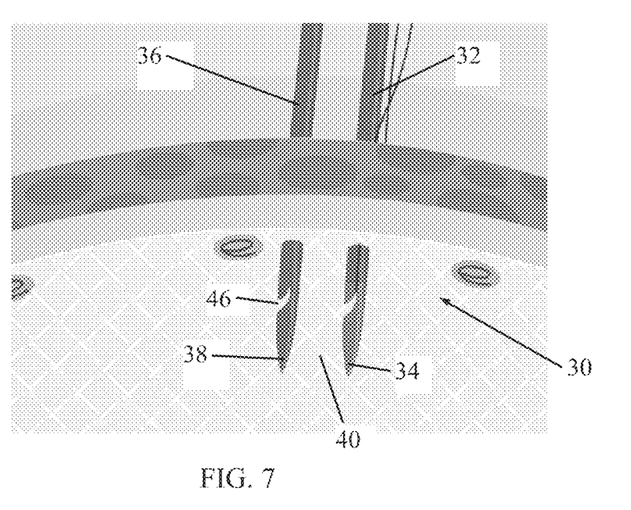
FIG. 7 is a simplified illustration of the mesh stitcher inserted to the abdominal wall, with stitcher needles (puncture elements) simultaneously penetrating the abdominal wall, in accordance with an embodiment of the present invention.
Figure 8:
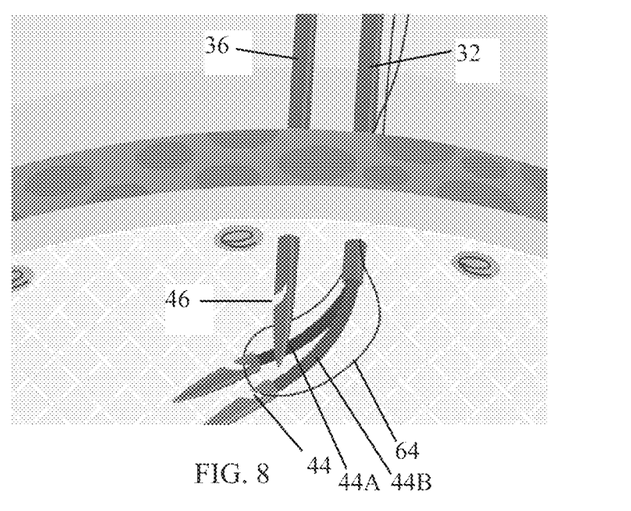
FIG. 8 is a simplified illustration of a suture passing from one needle to the other, with a one-handed manipulation of the stitcher, in accordance with an embodiment of the present invention.

FIG. 7 illustrates mesh stitcher 30 inserted to the abdominal wall, with puncture elements (needles) 32 and 36 simultaneously penetrating the abdominal wall. In the non-limiting illustrated embodiment, as seen in FIG. 8, the distal end of suture thread receiving member 44 is split or forked into two distal portions 44A and 44B. The rest of suture thread receiving member 44 is a rod that passes through first puncture element 32. Both portions 44A and 44B have a groove for receiving therein the suture 64. Suture thread receiving member 44 (or at least portions 44A and 44B) is made of a flexible resilient material, such as but not limited to, NITINOL. In this manner, when suture thread receiving member 44 is moved distally out of first puncture element 32, the spring energy (and/or shape memory) of the resilient body urges distal portions 44A and 44B to protrude out of first puncture element 32 and bend towards the distal end of suture grabber 46. The distal portions 44A and 44B are arranged so that they straddle the distal end of suture grabber 46. In other words, the distal end of suture grabber 46 is between distal portions 44A and 44B. In this manner, suture 64 easily passes from one needle to the other, with a one-handed manipulation of the stitcher.

Figure 9:
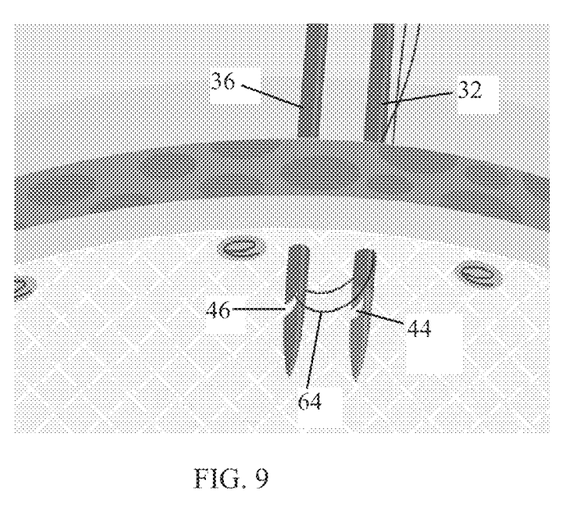
FIG. 9 is a simplified illustration of making the stitch, in accordance with an embodiment of the present invention.
Figure 10:
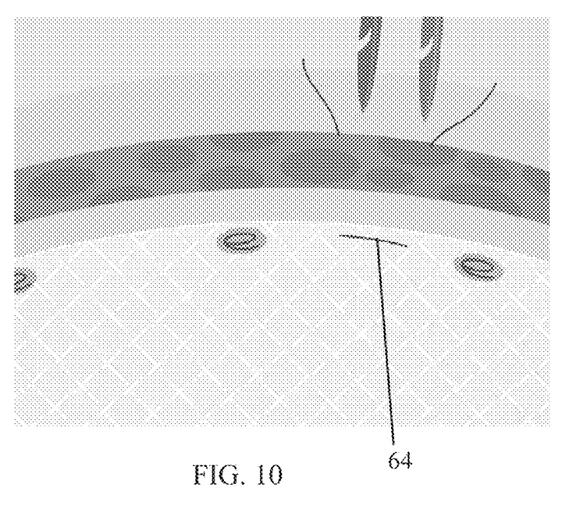
FIG. 10 is a simplified illustration of removing the mesh stitcher from the suture site.

FIG. 9 illustrates making the stitch, wherein distal portions 44A and 44B have been retracted back into first puncture element 32. FIG. 10 illustrates removing the mesh stitcher from the suture site.

Accordingly, the mesh stitcher 30 is a dual-action stitching device that makes precise laparoscopic mesh transfacial fixation faster and easier. Using one hand, the surgeon can pass the suture from one arm of the mesh stitcher 30 to the other, creating a stitch in three quick moves. The device allows the surgeon to quickly secure even a large mesh. It can be used to close trocar sites as well.

Reference is now made to FIGS. 11A-11D, which illustrate a mesh tacker 70, constructed and operative in accordance with an embodiment of the present invention, which is part of the kit and method for mesh deployment of the present invention.

Mesh tacker 70 may be similar in construction to the suture assembly described in copending U.S. patent application Ser. No. 12/427,778, the disclosure of which is incorporated herein by reference.

Tacker 70 may include a handle 72 with a first trigger assembly 74 and a second trigger assembly 76. Both trigger assemblies 74 and 76 are coupled to an articulated applicator arm 78 which is disposed through a drive shaft 80. The first trigger assembly 74 is used to apply rotary tacks (not shown in these figures) from a distal end 82 of applicator arm 78. This is accomplished by squeezing a trigger 84 towards the body of handle 72 (as shown by comparing FIGS. 11C and 11D). The second trigger assembly 76 is used to bend the distal end 82 of applicator arm 78 up (FIG. 11A) or down (FIG. 11B).

Figure 11A:
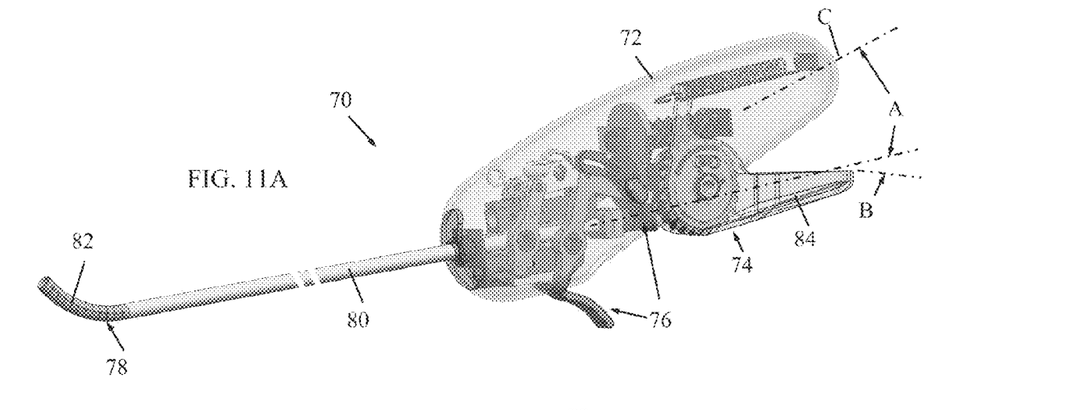
FIGS. 11A-11D are simplified pictorial illustrations of a mesh tacker, constructed and operative in accordance with an embodiment of the present invention, which is part of the kit and method for mesh deployment of the present invention.
Figure 11B:
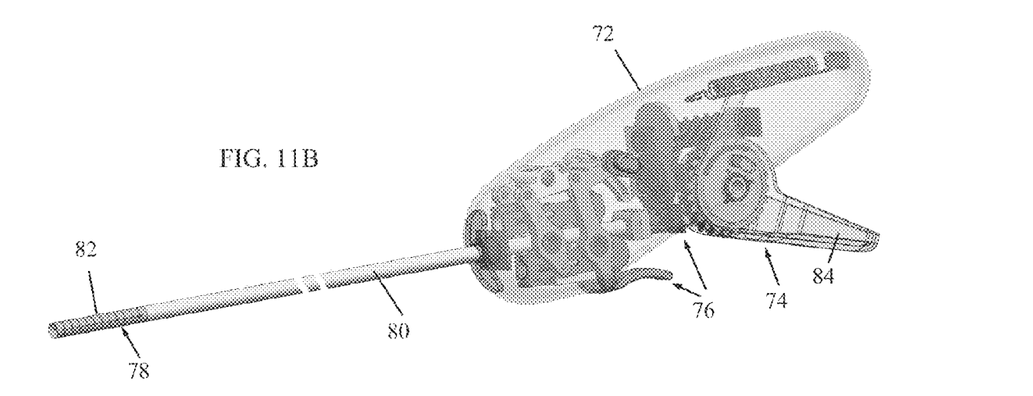
Figure 11C:
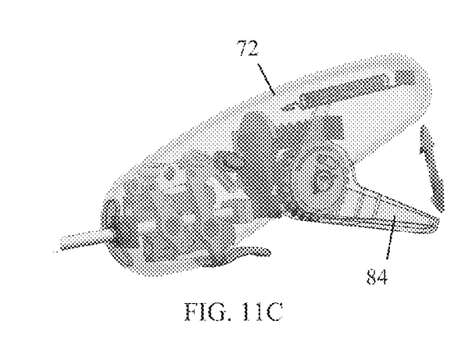
Figure 11D:
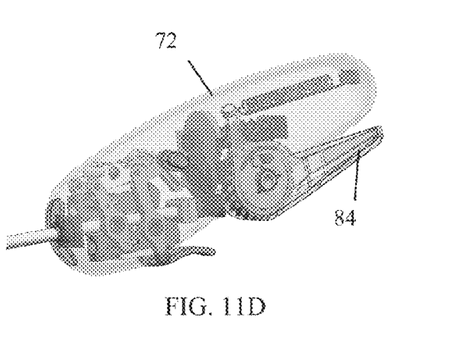

The central (longitudinal) axis C of handle 72 is tilted at an angle A in the range of about 7-25°, preferably about 77°, with respect to drive shaft 80 (that is, with respect to the proximal portion of applicator arm 78 which remains unbent), as seen in FIG. 11A. The tilted configuration of handle 72 is an important ergonomic feature of tacker 70. Prior art tackers have a pistol grip handle wherein the longitudinal axis of the handle is aligned or parallel with the drive shaft; there is no tilt. The prior art tacker is more cumbersome to use and can cause fatigue to the user. With the tilt of the present invention, tacker 70 is significantly more comfortable to use than prior art tackers. Another ergonomic feature is that trigger 84 is tilted at an angle B in the range of about 7-25°, preferably about 76°, with respect to drive shaft 80.

The angling tip and in-line handle of mesh tacker 70 enable a secure tack fixation angle through fewer trocars, leading to improved outcomes and optimal patient care. The angulation of mesh tacker 70 (the articulating tip) allows fixation of the mesh 360° from one side, and enables tacking from both the lateral and contralateral sides, and reaching difficult positions. This reduces or eliminates the need for placing additional trocars on the contralateral side. The in-line handle provides a more ergonomic design that reduces stress and increases surgeon comfort throughout the entire fixation process.

Mesh tacker 70 can be loaded in an angled position for intraoperative efficiency. The tacks are absorbable (see below) and longer than other available tacks. The additional length of the tack and the angulating tip of the tacker help provide the laparoscopic surgeon more consistent and secure mesh fixation.

Figure 12:
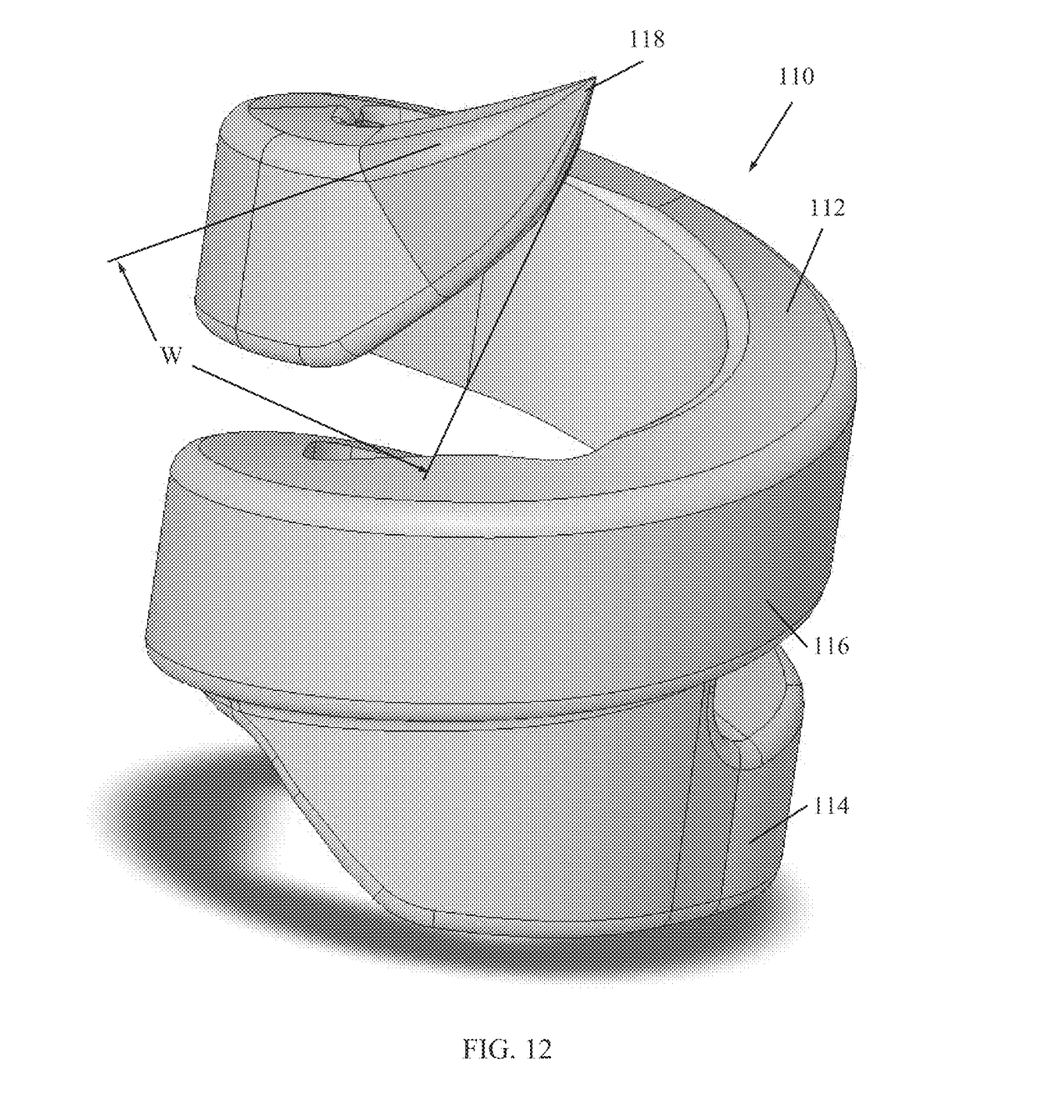
FIG. 12 is a simplified pictorial illustration of a rotary tack for use with the mesh tacker, constructed and operative in accordance with an embodiment of the present invention.

Reference is now made to FIG. 12, which illustrates a rotary tack 110, constructed and operative in accordance with an embodiment of the present invention, which is part of the kit and method for mesh deployment of the present invention.

Rotary tack 110 may be similar in construction to the suture assembly described in copending U.S. patent application Ser. No. 12/427,780, the disclosure of which is incorporated herein by reference.

Rotary tack 110 is preferably constructed of a resorbable material. Tack 110 may be constructed, without limitation, from a biodegradable polymer or copolymer of a type selected in accordance with the desired degradation time. A common biodegradable polymer used in absorbable sutures and the like is poly(L-lactide) which has a degradation time of about twelve to eighteen months. Without limitation, the tack may be constructed from an absorbable copolymer derived from glycolic and lactic acids, such as a synthetic polyester chemically similar to other commercial available glycolide and lactide copolymers. Glycolide and lactide, in vivo, degrade and absorb by hydrolysis into lactic acid and glycolic acid which are then metabolized by the body.

In accordance with a non-limiting embodiment of the present invention, tack 110 includes a helical body 112 having a closed-loop base 114 and a helix of spiral coils 116 that extend from base 114 and which terminate in a tip 118 for piercing tissue (not shown). In prior art helical fasteners, the base is open, that is, the lowermost coil is not a continuous closed coil or loop. In contrast, in the present invention, base 114 is closed. This geometry provides tack 110 with superior strength, especially important for use with the resorbable material. Tip 118 has a sharp edge at a wide angle W aimed upwards relative to the helix. Angle W is much greater than the helix angle of the coils.

The invention thus provides a kit for tissue repair, including mesh placer 10, mesh stitcher 30 and mesh tacker 70 (and may also include rotary tacks 110). The kit makes laparoscopic hernia repair (or other tissue repair) more consistent and efficient than the prior art.

A preferred method of using the kit includes first placing the mesh at the hernia repair site with the mesh placer, as described above. The surgeon can operate the mesh placer with just one hand to place the mesh at the desired position and angular orientation. Afterwards, the surgeon may use his/her other hand to grasp the mesh placer and hold the mesh in place. This frees the dexterous hand of the surgeon for the next step (of course, if the surgeon is ambidextrous, there is no need to switch hands). In the next step, the surgeon fastens the mesh to the tissue at the repair site. Fastening the mesh may be done by tacking the mesh to tissue with the mesh tacker using rotary tacks and/or by stitching the mesh to tissue with the mesh stitcher. Depending on the situation, the mesh may be fastened only with tacks, only with stitches, or any combination thereof. Although in most procedures, the mesh is first tacked and then stitched, the stitching and tacking may be done in any order. The stitching and tacking are done with the mesh stitcher and mesh tacker, respectively, as described above.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A kit for tissue repair comprising:
(A) a mesh placer comprising an application member configured to articulate with respect to a deployment rod, a mesh being attached to said application member;
(B) a mesh stitcher for stitching the mesh to tissue, comprising:
a first puncture element comprising a sharp distal end for puncturing tissue;
a second puncture element comprising a sharp distal end for puncturing tissue, the distal ends of said first and second puncture elements being spaced from each other by a gap;
suture thread disposed along a portion of said first puncture element, wherein said suture thread is arranged to be grabbed at the distal end of said first puncture element; and
a suture grabber positioned at the distal end of said second puncture element, said suture grabber having a mode of operation wherein:
a. said first puncture element is configured to puncture through a tissue wall so that said suture thread is configured to pass from a near side of said tissue wall to a far side of said tissue wall;
b. said second puncture element is configured to puncture through the tissue wall from said near side to said far side of said tissue wall; and
c. said suture grabber is configured to grab said suture thread at the distal end of said first puncture element at the far side of said tissue wall, bring said suture thread across said gap and move said suture thread proximally away from the distal end of said second puncture element back through to the near side of said tissue wall; and
(C) a tacker for applying a rotary tack for tacking the mesh to tissue comprising:
a handle with a first trigger assembly and a second trigger assembly, said first and second trigger assemblies being coupled to an articulated applicator arm which is disposed through a drive shaft connected to said handle, said first trigger assembly operative to apply a rotary tack from a distal end of said applicator arm and said second trigger assembly operative to bend said distal end of said applicator arm, wherein a longitudinal axis of said handle is tilted with respect to said drive shaft.

2. The kit according to claim 1, wherein said suture grabber is manipulatable by a manipulator operable by one hand.

3. The kit according to claim 1, further comprising a rotary tack disposed on said applicator arm.

4. The kit according to claim 3, wherein said rotary tack comprises a helical body constructed of a resorbable material.

* * * * *